United States Patent
Thatipally et al.

(10) Patent No.: US 9,573,902 B2
(45) Date of Patent: Feb. 21, 2017

(54) PROCESS FOR THE PREPARATION OF IVACAFTOR AND ITS INTERMEDIATES

(71) Applicant: Laurus Labs Private Limited, Hyderabad (IN)

(72) Inventors: Suresh Thatipally, Hyderabad (IN); Venkata Lakshmi Narasimha Rao Dammalapati, Hyderabad (IN); Seeta Ramanjaneyulu Gorantla, Hyderabad (IN); Satyanarayana Chava, Hyderabad (IN)

(73) Assignee: LAURUS LABS PRIVATE LTD., Hyderabad (IN)

( * ) Notice: Subject to any disclaimer, the term of this patent is extended or adjusted under 35 U.S.C. 154(b) by 0 days.

(21) Appl. No.: 14/768,082

(22) PCT Filed: Feb. 14, 2014

(86) PCT No.: PCT/IN2014/000096
§ 371 (c)(1),
(2) Date: Aug. 14, 2015

(87) PCT Pub. No.: WO2014/125506
PCT Pub. Date: Aug. 21, 2014

(65) Prior Publication Data
US 2016/0016909 A1    Jan. 21, 2016

(30) Foreign Application Priority Data
Feb. 15, 2013  (IN) ............... 690/CHE/2013

(51) Int. Cl.
*A61K 31/47*  (2006.01)
*C07D 215/56*  (2006.01)
*C07D 215/48*  (2006.01)
*C07C 227/14*  (2006.01)
*C07C 227/18*  (2006.01)
*C07C 229/30*  (2006.01)

(52) U.S. Cl.
CPC ............. *C07D 215/56* (2013.01); *A61K 31/47* (2013.01); *C07C 227/14* (2013.01); *C07C 227/18* (2013.01); *C07C 229/30* (2013.01); *C07D 215/48* (2013.01)

(58) Field of Classification Search
CPC ..... A61K 31/47; C07D 215/48; C07C 227/14; C07C 227/18; C07C 229/30
See application file for complete search history.

(56) References Cited

U.S. PATENT DOCUMENTS

| | | |
|---|---|---|
| 7,495,103 B2 | 2/2009 | Hadida-Ruah et al. |
| 8,163,772 B2 | 4/2012 | DeMattei et al. |
| 2011/0064811 A1 | 3/2011 | Hurter et al. |
| 2011/0230519 A1 | 9/2011 | Arekar et al. |
| 2011/0267768 A1 | 11/2011 | Attlesey |
| 2013/0281487 A1 | 10/2013 | Luisi et al. |

FOREIGN PATENT DOCUMENTS

CN   103044263 A   4/2013

OTHER PUBLICATIONS

Ramsey, N Engl J MEd, vol. 365 (18), 1663-1672, 2011.*
Song, Formulary, vol. 47, 132-141, Apr. 2012.*
Reddy, Asian J of Chem, vol. 23(7), 2981-2988, 2011.*
Barbierikova, J Photochem and Photobiol A: Chemistry, 224, pp. 123-134, 2011.*

* cited by examiner

*Primary Examiner* — D M Seaman
(74) *Attorney, Agent, or Firm* — Blank Rome, LLP

(57) ABSTRACT

The present invention provides novel intermediates of ivacaftor and process for its preparation. The present invention also provides process for the preparation of ivacaftor and pharmaceutically acceptable salt thereof using novel intermediates.

23 Claims, No Drawings

PROCESS FOR THE PREPARATION OF IVACAFTOR AND ITS INTERMEDIATES

PRIORITY

This application is a national phase application of PCT/IN2014/000096, filed on Feb. 14, 2014, which claims the benefit under Indian Provisional Application No. 690/CHE/2013, filed on Feb. 15, 2013, the contents of which are incorporated by reference herein.

FIELD OF THE INVENTION

The present invention generally relates to a process for the preparation of Ivacaftor and pharmaceutically acceptable salts thereof. The present invention also relates to a process for the preparation of novel intermediates and their use in the preparation of ivacaftor.

BACKGROUND OF THE INVENTION

Ivacaftor, also known as N-(2,4-di-tert-butyl-5-hydroxyphenyl)-1,4-dihydro-4-oxoquinoline-3-carboxamide, having the following Formula I:

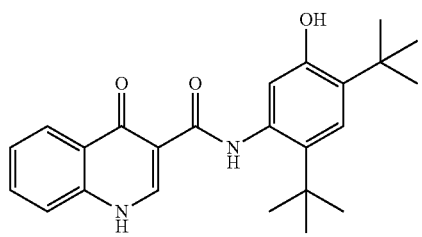

Formula I

Ivacaftor was approved by FDA and marketed by Vertex pharma for the treatment of cystic fibrosis under the brand name KALYDECO® in the form of 150 mg oral tablets.

U.S. Pat. No. 7,495,103 ("the '103 patent") discloses modulators of ATP-binding cassette transporters such as ivacaftor. The '103 patent further discloses a process for the preparation of modulators of ATP-binding cassette transporters such as quinoline compounds; however, ivacaftor process was not specifically disclosed. The '103 patent process includes condensation of 4-oxo-1,4-dihydro-3-quinoline carboxylic acid with aniline in presence of 2-(1H-7-azabenzotriazol-1-yl)-1,1,3,3-tetramethyluronium hexafluoro phosphate methanaminium (HATU) and then purifying the obtained compound by HPLC. The process disclosed in the '103 patent is schematically represented as follows:

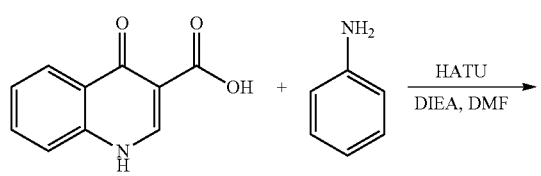

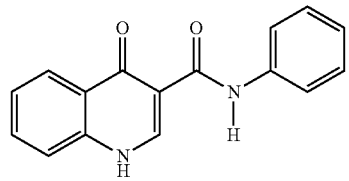

The '103 patent also discloses a process for the preparation of intermediates of ivacaftor such as 4-oxo-1,4-dihydro-3-quinoline carboxylic acid and 5-amino-2,4-di-(tert-butyl) phenol.

The process to prepare 4-oxo-1,4-dihydro-3-quinoline carboxylic acid involves the reaction of aniline with diethylethoxymethylene malonate followed by cyclization with large excess of polyphosphoric acid and phosphoryl chloride and then hydrolysis, which is schematically represented as follows:

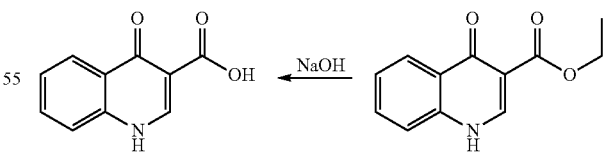

The process to prepare 5-amino-2,4-di-(tert-butyl)phenol involves hydroxyl protection followed by nitration, deprotection of the hydroxyl group and reduction of nitro group, which is schematically represented as follows:

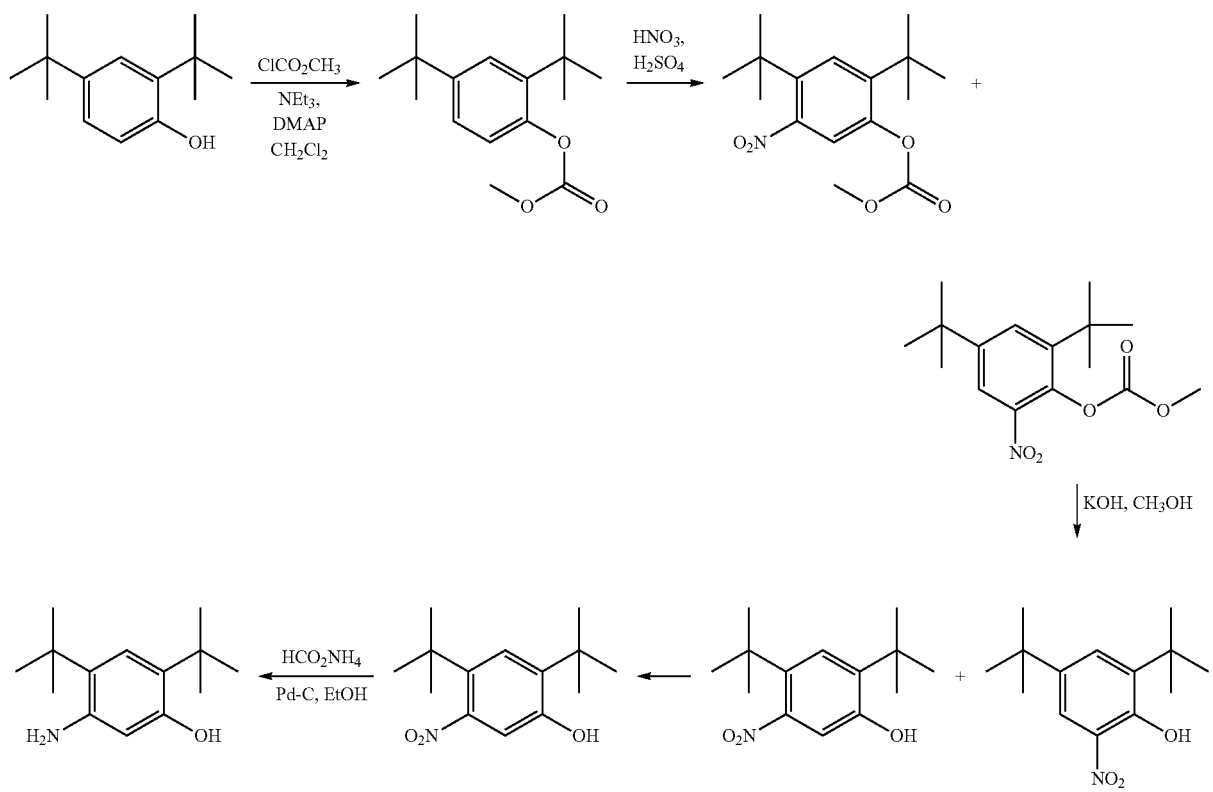

The synthesis of ivacaftor and its intermediates as discussed in the '103 patent has certain drawbacks as it involves:

a) use of tedious high performance liquid chromatography (HPLC) techniques for isolation of intermediates as well as final ivacaftor, makes the process quite expensive and not viable for large scale operations, and b) use of high temperature reactions and large excess of phosphoryl chloride and strong acids like poly phosphoric acid leads to load on environment, which makes the process more complex, costly and highly unattractive particularly on commercial scale operations.

U.S. Patent Publication No. 2011/230519 ("the '519 publication") discloses a process for preparation of 4-oxo-1,4-dihydro-3-quinoline carboxylic acid by reaction of aniline with diethylethoxymethylene malonate at 100-110° C. followed by cyclization in presence of phenyl ether at temperature 228-232° C. and hydrolysis, which is schematically represented as follows:

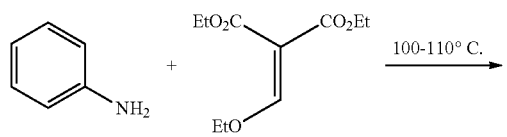

-continued

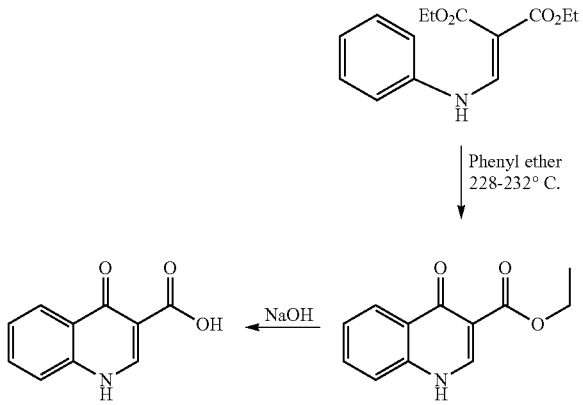

Disadvantages associated with the '519 publication is, usage of high temperature reactions such as cyclization at 228-232° C., which is difficult to achieve on large scale operations and further leads to the formation of unwanted by products and low product yields.

U.S. Patent Publication No. 2010/0267768 ("the '768 publication") discloses a process for preparation of ivacaftor, which involves the coupling of 4-oxo-1,4-dihydro-3-quinoline carboxylic acid with hydroxyl protected phenol intermediate in the presence of propyl phosphonic anhydride ($T_3P$®) followed by deprotection of hydroxyl protection group and optional crystallization with isopropyl acetate. The process disclosed in the '768 publication is schematically represented as follows:

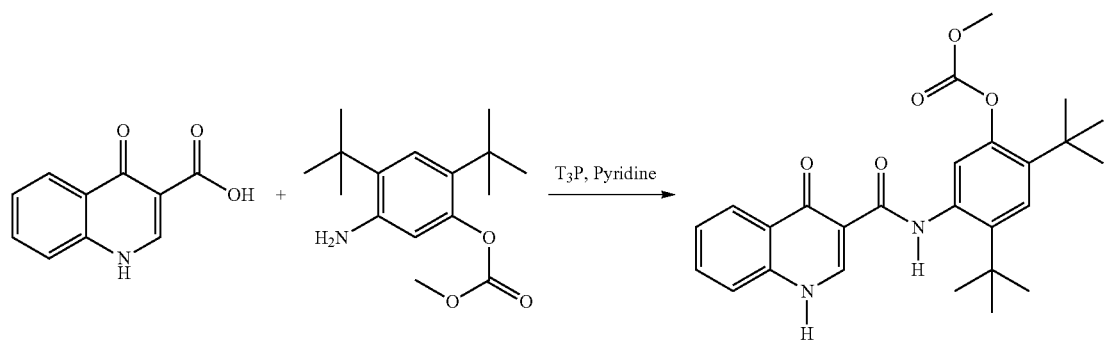

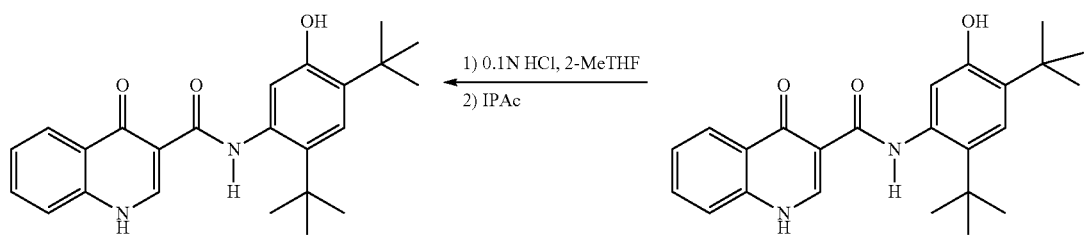

The '768 publication discloses the use of highly expensive coupling reagent, propyl phosphonic anhydride; which in turn result to an increase in the manufacturing cost.

U.S. Patent Publication No. 2011/064811 ("the '811 publication") discloses a process for preparation of ivacaftor, which involves condensation of 4-oxo-1,4-dihydro-3-quinoline carboxylic acid with 5-amino-2,4-di-(tert-butyl)phenol in the presence of HBTU followed by the formation of ethanol crystalate, which is then treated with diethyl ether to yield ivacaftor as a solid. The process disclosed in the '811 publication is schematically represented as follows:

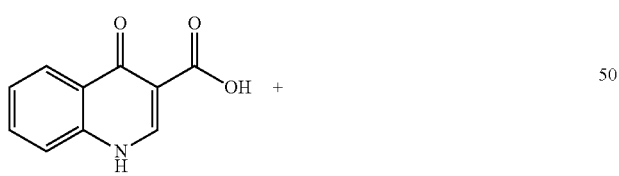

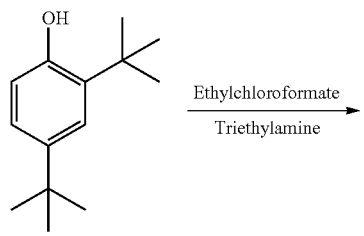

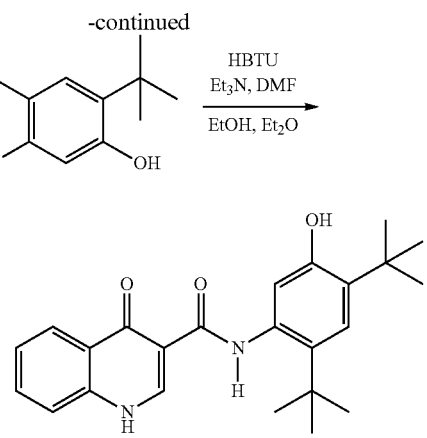

CN 103044263 discloses a process for the preparation of ivacaftor and the disclosed process schematically represented as follows:

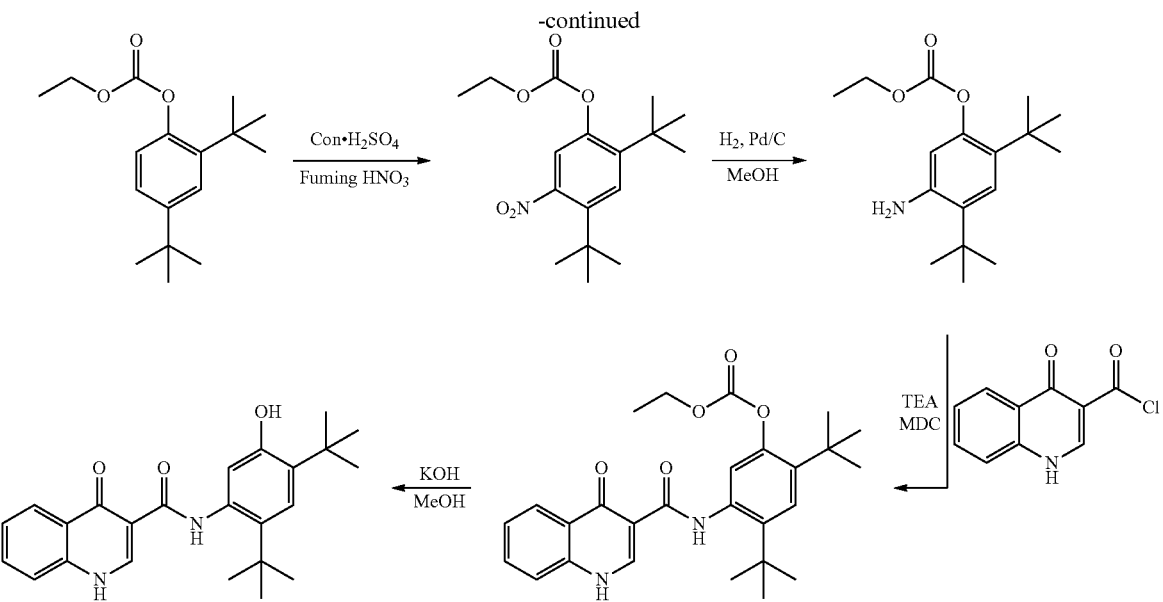

Ivacaftor can exist in different polymorphic forms, which differs from each other in terms of stability, physical properties, spectral data and methods of preparation.

The '811 publication discloses polymorphs of ivacaftor such as crystalline ethanol solvate, Form A, Form B and amorphous Form.

The '519 publication discloses crystalline polymorph of ivacaftor such as Form C and preparation thereof.

U.S. Pat. No. 8,163,772 ("the '772 patent") discloses solid forms of ivacaftor such as 2-methyl butyric acid (Form I), propylene glycol (Form II), PEG400.KOAc (Form III), lactic acid (Form IV), isobutyric acid (Form V), propionic acid (Form VI), ethanol (Form VII), 2-propanol (Form VIII), water (Form IX), besylate Form A (Form X), besylate Form B (Form XI), besylate Form D (Form XII), besylate Form E (Form XIII), besylate Form F (Form XIV), besylate Form A (Form X), hemibesylate (Form XV), and besylate monohydrate (Form XVI).

US Patent Publication No. 2013/281487 discloses crystalline solvates of ivacaftor, which are designated as Form D, Form E, Form F, Form G, Form H, Form I, Form J, Form K, Form L, Form M, Form N, Form O, Form P, Form Q, Form R, Form S, Form T, Form W and hydrate B. The said publication also disclosed process for their preparation.

It would be desirable to provide a process for the preparation of ivacaftor and intermediates thereof, which is simple and cost effective; in a convenient, cost efficient manner and a commercial scale.

The present invention provides a process for the preparation of ivacaftor using novel protected quinoline carboxylic acid compounds as intermediates, that process away from the aforementioned difficulties such as high temperature reactions and use of large excess of polyphosphoric acid and corrosive phosphoryl chloride are avoided. The process of the present invention can be practiced on an industrial scale, and also can be carried out without sacrifice of overall yield.

OBJECT OF THE INVENTION

The main object of the invention is to provide a simple, cost effective process for the preparation of ivacaftor and intermediates thereof.

Another object of the invention is to provide a process for the preparation of ivacaftor in high yield and purity by using novel protected quinoline carboxylic acid compounds as intermediates.

Yet another object of the invention is to provide a process for the preparation of ivacaftor in high yield and purity without involving high temperature reactions such as at about 150° C. and at about 230° C., to minimize the product degradation.

Further object of the invention is to provide a process for the preparation of ivacaftor, which avoids the usage of corrosive reagents such as polyphosphoric acid and phosphoryl chloride.

SUMMARY OF THE INVENTION

The present invention encompasses a process for the preparation of ivacaftor and its intermediates thereof. The present invention further encompasses a process for the preparation of ivacaftor using novel protected quinoline carboxylic acid compounds as intermediates.

In one embodiment, the present invention provides a process for the preparation of ivacaftor of Formula I,

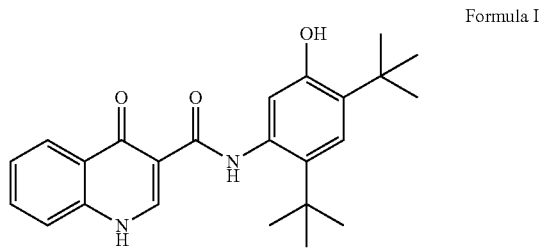 [SMILES: CC(C)(C)c1cc(C(C)(C)C)c(NC(=O)c2c[nH]c3ccccc3c2=O)cc1O]

Formula I comprising:
a) coupling a protected quinoline carboxylic acid compound of Formula IV or an ester thereof

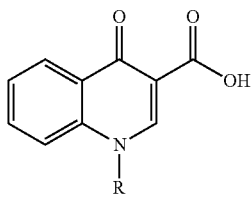
Formula IV wherein "R" represents a suitable cleavable group; with 5-amino-2,4-di-(tert-butyl) phenol of Formula III

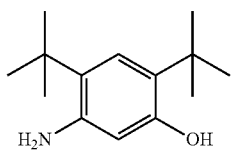
Formula III in presence of a coupling reagent optionally in presence of a base to obtain a protected ivacaftor compound of Formula II

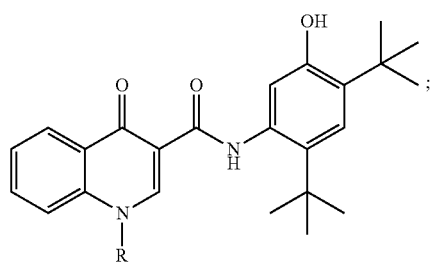
Formula II and b) deprotecting the resulting protected ivacaftor compound of Formula II.

In a second embodiment, the present invention provides a process for the preparation of ivacaftor of Formula I, comprising:

a) coupling a protected quinoline carboxylic acid compound of Formula IV or an ester thereof, wherein "R" represents an aralkyl, alkyl group and the like, optionally substituted with one or more groups selected from halo, nitro, cyano, amino, hydroxyl, alkyl, halo alkyl or alkoxy; with 5-amino-2,4-di-(tert-butyl)phenol of Formula III in presence of a coupling reagent optionally in presence of a base to obtain a protected ivacaftor compound of Formula II; and b) deprotecting the resulting protected ivacaftor compound of Formula II.

In a third embodiment, the present invention provides a process for the preparation of ivacaftor of Formula I, comprising:

i) condensing 2-fluorobenzoic acid or a reactive derivative thereof of Formula IX

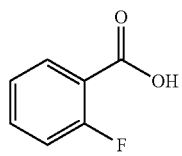
Formula IX with acrylate compound of Formula VIII

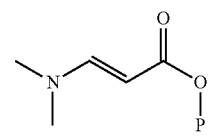
Formula VIII wherein "P" represents H or $C_{1-4}$ alkyl; to obtain a compound of Formula VII,

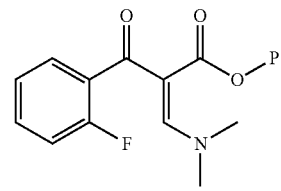
Formula VII wherein "P" is defined as above, ii) reacting the compound of Formula VII with an amine of formula, R—NH$_2$,
wherein "R" represents an aralkyl, alkyl group and the like, optionally substituted with one or more groups selected from halo, nitro, cyano, amino, hydroxyl, alkyl, halo alkyl or alkoxy; to obtain a compound of Formula VI, Formula VI wherein "R" and "P" are defined as above;

iii) cyclizing the compound of Formula VI in presence of a base to obtain a compound of Formula V, wherein "R" and "P" are defined as above;

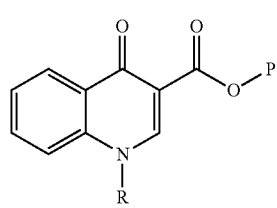
Formula V iv) hydrolyzing the compound of Formula V with a base to obtain a protected quinoline carboxylic acid compound of Formula IV, wherein "R" is defined as above,

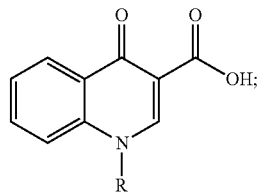

Formula IV and v) converting the protected quinoline carboxylic acid compound of Formula IV in to ivacaftor of Formula I.

In a fourth embodiment, the present invention provides an intermediate compound of Formula VI,

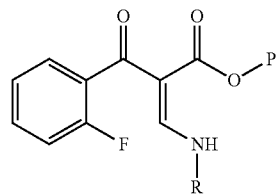

Formula VI wherein "P" represents H or $C_{1-4}$ alkyl and "R" represents a suitable cleavable group.

In a fifth embodiment, the present invention provides an intermediate compound of Formula VI, wherein "P" represents H or $C_{1-4}$ alkyl such as methyl, ethyl, isopropyl and the like; "R" represents a suitable cleavable group selected from aralkyl, alkyl and the like, optionally substituted with one or more groups selected from halo, nitro, cyano, amino, hydroxyl, alkyl, halo alkyl or alkoxy.

In a sixth embodiment, the present invention provides an intermediate compound of Formula V,

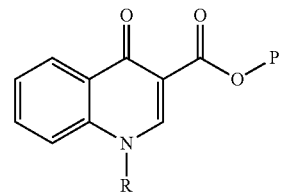

Formula V wherein "P" represents H or $C_{1-4}$ alkyl and "R" represents a suitable cleavable group.

In a seventh embodiment, the present invention provides an intermediate compound of Formula V, wherein "P" represents H or $C_{1-4}$ alkyl such as methyl, ethyl, isopropyl and the like; "R" represents a suitable cleavable group selected from aralkyl, alkyl and the like, optionally substituted with one or more groups selected from halo, nitro, cyano, amino, hydroxyl, alkyl, halo alkyl or alkoxy.

In an eighth embodiment, the present invention provides an intermediate compound of Formula IV,

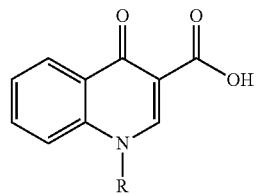

Formula IV wherein "R" represents a suitable cleavable group.

In a ninth embodiment, the present invention provides an intermediate compound of Formula IV, wherein "R" represents a suitable cleavable group selected from aralkyl, alkyl and the like, optionally substituted with one or more groups selected from halo, nitro, cyano, amino, hydroxyl, alkyl, halo alkyl or alkoxy.

In a tenth embodiment, the present invention provides an intermediate compound of Formula II,

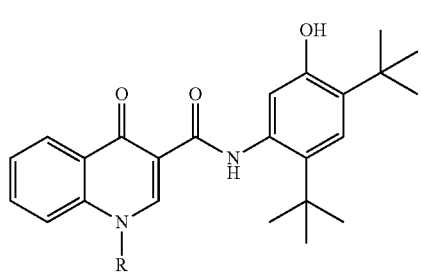

Formula II wherein "R" represents a suitable cleavable group.

In an eleventh embodiment, the present invention provides an intermediate compound of Formula II, wherein "R" represents a suitable cleavable group selected from aralkyl, alkyl and the like, optionally substituted with one or more groups selected from halo, nitro, cyano, amino, hydroxyl, alkyl, halo alkyl or alkoxy.

In a twelfth embodiment, the present invention provides a process for the preparation of ivacaftor of formula I, comprising:
a) condensing 2-fluoro benzoyl chloride with ethyl-3-N,N-dimethyl amino acrylate to obtain ethyl-3-(dimethylamino)-2-(2-fluorobenzoyl)-2-propenoate,
b) reacting the ethyl-3-(dimethylamino)-2-(2-fluorobenzoyl)-2-propenoate with benzylamine to obtain ethyl-3-(benzylamino)-2-(2-fluorobenzoyl)-2-propenoate,
c) cyclizing the ethyl-3-(benzylamino)-2-(2-fluorobenzoyl)-2-propenoate in presence of a base to obtain ethyl-1-benzyl-4-oxo-1,4-dihydroquinoline-3-carboxylate,
d) hydrolyzing the ethyl-1-benzyl-4-oxo-1,4-dihydroquinoline-3-carboxylate with a base to obtain 1-benzyl-4-oxo-1,4-dihydroquinoline-3-carboxylic acid,
e) coupling the 1-benzyl-4-oxo-1,4-dihydroquinoline-3-carboxylic acid with 5-amino-2,4-di-(tert-butyl) phenol in presence of a coupling reagent and a base to obtain N-(2,4-di-tert-butyl-5-hydroxyphenyl)-1-benzyl-4-oxo-1,4-dihydroquinoline-3-carboxamide; and
f) deprotecting the N-(2,4-di-tert-butyl-5-hydroxyphenyl)-1-benzyl-4-oxo-1,4-dihydroquinoline-3-carboxamide to obtain ivacaftor.

In a thirteenth embodiment, the present invention provides a pharmaceutical composition comprising ivacaftor or a pharmaceutically acceptable salt thereof prepared by the processes of the present invention and at least one pharmaceutically acceptable excipient.

DETAILED DESCRIPTION OF THE INVENTION

The present invention provides a process for the preparation of ivacaftor and its intermediates thereof with high product yield and quality. In particular, the present invention provides a process for the preparation of ivacaftor wherein the process includes the use of novel protected quinoline carboxylic acid compounds as intermediates, which avoids high temperature reactions and usage of corrosive reagents such as polyphosphoric acid and phosphoryl chloride; thereby process more convenient and economical, particularly on commercial scale.

Unless otherwise specified, the term "suitable cleavable group" used herein the specification includes but are not limited to alkyl, aralkyl and the like, optionally substituted with one or more groups selected from halo, nitro, cyano, amino, hydroxyl, alkyl, halo alkyl or alkoxy.

Unless otherwise specified, the term "alkyl" used herein the specification includes, but are not limited to methyl, ethyl, isopropyl, 1-butyl, n-butyl, t-butyl, 2-methyl-1-propanol, pentyl, 2-pentyl, 3-pentyl, hexyl, heptyl, octyl and the like.

Unless otherwise specified, the term "aralkyl" used herein the specification includes but not limited to benzyl, 1-phenylethyl, 2-phenylethyl and the like.

In one embodiment, the present invention provides a process for preparation of ivacaftor of Formula I, comprising:

a) coupling a protected quinoline carboxylic acid compound of Formula IV or an ester thereof

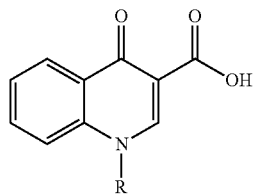

Formula IV wherein "R" represents a suitable cleavable group; with 5-amino-2,4-di-(tert-butyl) phenol of Formula III

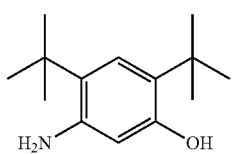

Formula III in presence of a coupling reagent optionally in presence of a base to obtain a protected ivacaftor compound of Formula II,

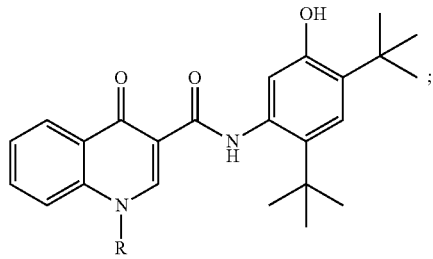

Formula II and
b) deprotecting the resulting protected ivacaftor compound of Formula II.

5-amino-2,4-di-(tert-butyl)phenol of Formula III is known in the art and can be prepared by any known method, for example may be synthesized as per the process disclosed in U.S. Pat. No. 7,495,103.

Step a) of the forgoing process involves coupling of protected quinoline carboxylic acid compound of Formula IV or an ester thereof, wherein "R" is a suitable cleavable group, with 5-amino-2,4-di-(tert-butyl)phenol of Formula III to obtain a protected ivacaftor of Formula II includes: admixing the protected quinoline carboxylic acid compound of Formula IV in an organic solvent with a base, 5-amino-2,4-di-(tert-butyl)phenol and a coupling regent at a temperature of about ambient temperature to about reflux.

Preferably the suitable cleavable group is substituted or unsubstituted benzyl; wherein the substituent are selected from halo, nitro, cyano, amino, hydroxyl, alkyl, halo alkyl or alkoxy; more preferably suitable cleavable group is selected from benzyl, 4-methoxy benzyl, 4-trifluoromethyl benzyl, 4-chloro benzyl and the like; and most preferably benzyl.

The coupling agent used herein the reaction may be selected from any coupling agent known in the art. For example, HATU (1-[Bis(dimethylamino)methylene]-1H-1,2,3-triazolo[4,5-b]pyridinium 3-oxid hexafluorophosphate) or HBTU (O-Benzotriazole-N,N,N',N'-tetramethyl-uronium-hexafluoro-phosphate).

The base is selected from organic base such as methyl amine, ethyl amine, dimethylamine, diethylamine, triethylamine, tripropylamine, triisopropylamine, tributylamine, triisobutylamine, N,N-diisopropylethylamine, N,N-dimethylaniline, N,N-dimethyl aminopyridine and the like and mixtures thereof; an inorganic base such as sodium hydroxide, potassium hydroxide, lithium hydroxide, sodium carbonate, potassium carbonate, lithium carbonate, sodium bicarbonate, potassium bicarbonate, ammonia and the like; and mixtures thereof. Preferably the base used is organic base and more preferably N,N-diisopropylethylamine.

The organic solvent used in the coupling reaction includes, but are not limited to alcohols, ethers, esters, nitriles, ketones, amides. The alcohols include, but are not limited to methanol, ethanol, isopropanol, n-propanol, n-butanol, isobutanol, t-butanol and the like; the ethers include, but are not limited to dimethyl ether, diethyl ether, methyl ethyl ether, diisopropyl ether, methyl tertiary butyl ether, tetrahydrofuran, 1,4-dioxane and the like; the esters include, but are not limited to ethyl acetate, isopropyl acetate, isobutyl acetate and the like; the niriles include, but are not limited to acetonitrile, propionitrile and the like; the amides include, but are not limited to dimethyl formamide, dimethyl acetamide, N-methyl pyrrolidinone and the like; and mixtures thereof. Preferably the solvent used is amides and more preferably dimethylformamide.

The reaction temperature should be sufficient to effect the coupling reaction. Typically the reaction temperature may be from about ambient temperature to about reflux temperature of the solvent used; preferably about 20° C. to about 85° C.; more preferably at about 25° C. to about 35° C.

Step b) of the forgoing process involves the deprotection of protected ivacaftor compound of Formula II, wherein "R" is suitable cleavable group as defined above, may be carried out with a suitable deprotecting agent in a suitable solvent. The suitable deprotecting agent includes, but is not limited to palladium, palladium hydroxide, raney nickel, hydrazine and the like optionally in presence of a hydrogen source selected from hydrogen, ammonium formate and the like. Preferably the deprotecting agent used is palladium hydroxide in presence of ammonium formate.

The deprotection compound of Formula II, wherein "R" is an alkyl then the suitable deprotecting agent is an acid and is selected from the group consisting of hydrochloric acid, hydrobromic acid, trifluoro acetic acid and the like and mixtures thereof.

The suitable solvent for deprotection includes, but is not limited to alcohols, amides, nitriles and the like. The alcohols include, but are not limited to methanol, ethanol, isopropanol, n-propanol, n-butanol, isobutanol, t-butanol and the like; the amides include, but are not limited to dimethyl formamide, dimethyl acetamide, N-methyl pyrrolidinone and the like; the nitriles include, but are not limited to acetonitrile, propionitrile and the like; and mixtures thereof. Preferably the solvent used is amides and more preferably dimethylformamide.

The deprotection reaction may be performed at ambient temperature to about reflux temperature, preferably at about 40° C. to about 110° C.; more preferably at about 70° C. to about 80° C.

In another embodiment, the present invention provides an intermediate compound of Formula II,

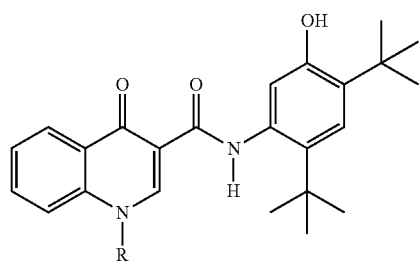

Formula II wherein "R" represents suitable cleavable group selected from aralkyl, alkyl and the like, optionally substituted with one or more groups selected from halo, nitro, cyano, amino, hydroxyl, alkyl, halo alkyl or alkoxy; preferably aralkyl includes, but are not limited to benzyl, 4-methoxy benzyl, 4-trifluoromethyl benzyl, 4-chloro benzyl and the like; and the alkyl includes, but are not limited to methyl, ethyl, isopropyl, 1-butyl, n-butyl, t-butyl, 2-methyl-1-propanol, pentyl, 2-pentyl, 3-pentyl, hexyl, heptyl, octyl and the like; more preferably R is benzyl.

In a preferred embodiment, the present invention provides an intermediate compound of Formula IIA.

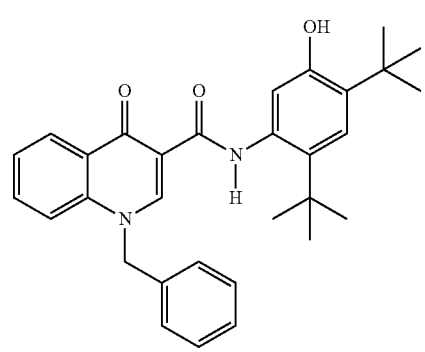

Formula IIA

In another embodiment, the present invention provides a process for preparation of ivacaftor of Formula I, comprising:

i) condensing 2-fluorobenzoic acid or a reactive derivative thereof of Formula IX

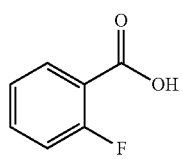

Formula IX with acrylate compound of Formula VIII

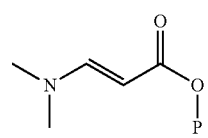

Formula VIII wherein "P" represents H or $C_{1-4}$ alkyl; to obtain a compound of Formula VII,

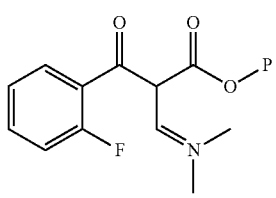

Formula VII wherein "P" is defined as above, ii) reacting the compound of Formula VII with an amine of formula, R—NH$_2$, wherein "R" represents an aralkyl, alkyl group and the like, optionally substituted with one or more groups selected from halo, nitro, cyano, amino, hydroxyl, alkyl, halo alkyl or alkoxy; to obtain a compound of Formula VI,

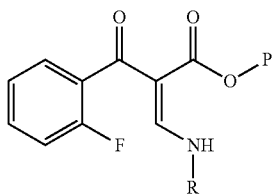

Formula VI wherein "R" and "P" are defined as above;

iii) cyclizing the compound of Formula VI in presence of a base to obtain a compound of Formula V, wherein "R" and "P" are defined as above;

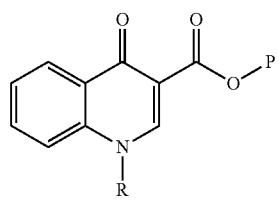

Formula V iv) hydrolyzing the compound of formula V with a base to obtain a protected quinoline carboxylic acid compound of Formula IV, wherein "R" is defined as above,

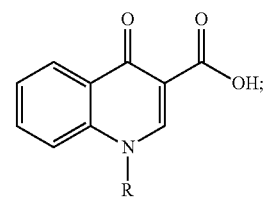

Formula IV and v) converting the protected quinoline carboxylic acid compound of Formula IV in to ivacaftor of Formula I.

The starting material, 2-fluorobenzoic acid of Formula IX and acrylate compound of Formula VIII are known in the art and are commercially available.

Preferably the 2-fluorobenzoic acid of Formula IX is taken as its reactive derivative, preferably a chloro derivative, which is prepared by a known process, for instance the 2-fluorobenzoic acid is treated with thionyl chloride and the resulting compound is used in-situ for further reaction.

Step i) of condensing 2-fluorobenzoic acid or a reactive derivative, preferably chloro derivative with acrylate compound of Formula VIII, wherein "P" is $C_{1-4}$ alkyl such as methyl, ethyl, isopropyl and the like; preferably ethyl, includes: reacting the mixture of acrylate compound of Formula VIII and a base in an organic solvent with 2-fluobenzoyl chloride at a temperature of about ambient temperature to about reflux to obtain a compound of Formula VII, wherein "P" is ethyl group.

The organic solvent includes, but is not limited to halogenated hydrocarbons, aromatic hydrocarbons, ethers, amides, nitriles and the like and mixtures thereof. The halogenated hydrocarbons include, but are not limited to methylene chloride, ethylene chloride, chloroform, carbon tetrachloride and the like and mixtures thereof; aromatic hydrocarbons include, but are not limited to toluene, xylene, chlorobenzene and the like and mixtures thereof; ethers include, but are not limited to dimethyl ether, diethyl ether, methyl ethyl ether, diisopropyl ether, methyl tertiary butyl ether, tetrahydrofuran, 1,4-dioxane and the like and mixtures thereof; amides include, but are not limited to dimethyl formamide, dimethyl acetamide, N-methyl pyrrolidinone and the like and mixtures thereof; nitriles include, but are not limited to acetonitrile, propionitrile and the like and mixtures thereof. Preferably the solvent used is aromatic hydrocarbon and more preferably toluene.

The base used is either selected from organic base such as methyl amine, ethyl amine, dimethylamine, diethylamine, triethylamine, N,N-diisopropylethylamine, N,N-dimethylaniline, N,N-dimethyl aminopyridine and the like; or inorganic base such as sodium hydroxide, potassium hydroxide, lithium hydroxide, sodium carbonate, potassium carbonate, lithium carbonate, sodium bicarbonate, potassium bicarbonate, ammonia and the like; and mixtures thereof. Preferably, the base used is an organic base and more preferably triethylamine.

The reaction temperature is suitable for step i) is about ambient temperature to about reflux, preferably at about 40° C. to about 125° C.; more preferably at about 50° C. to about 55° C.

Step ii) of reacting the compound of Formula VII, wherein "P" is ethyl, with an amine of formula, R—NH$_2$; wherein R is defined as above, preferably the amine of formula "R—NH$_2$" includes, but are not limited to benzylamine, 4-methoxy benzylamine, 4-trifluoromethyl benzylamine, 4-chloro benzylamine, ethylamine, isopropylamine, n-butylamine, tert-butylamine, pentylamine, 2-aminopentane, 3-aminopentane, hexylamine, 2-aminohexane, 3-aminohexane, heptylamine, 2-aminoheptane, 3-amino heptanes, 4-aminoheptane, octylamine, 2-amino octane, 3-aminooctane, 4-aminooctane, 2-amino-1-ethanol, 2-amino-2-methyl-1-propanol, 3-amino-1-butanol; more preferably benzyl amine (i.e., R is benzyl), in an organic solvent to obtain a compound of Formula VI, wherein "R" is benzyl and "P" is ethyl group.

The organic solvent used in step ii) includes, but is not limited to halogenated hydrocarbons, aromatic hydrocarbons, ethers, amides, nitriles and the like and mixtures thereof; preferably toluene, xylene, chlorobenzene, methylene chloride, chloroform, diisopropyl ether, methyl tert butyl ether, dimethyl formamide, acetonitrile and the like; and mixtures thereof; more preferably toluene.

The reaction temperature should be sufficient to effect the step ii) reaction. Typically the reaction temperature may be from about ambient temperature to about reflux temperature; preferably about 20° C. to about 85° C.; more preferably at about 25° C. to about 45° C.

Step iii) of aforementioned process involves cyclizing the compound of Formula VI, wherein "R" is benzyl and "P" is ethyl, in presence of a base to obtain a compound of Formula V, wherein "R" and "P" are defined as above.

Preferably the base used for the cyclization of compound Formula VI includes, but is not limited to organic base such as methyl amine, ethyl amine, dimethylamine, diethylamine, triethylamine, N,N-diisopropylethylamine, N,N-dimethylaniline, N,N-dimethyl aminopyridine and the like; an inorganic base such as sodium hydroxide, potassium hydroxide, lithium hydroxide, sodium carbonate, potassium carbonate, lithium carbonate, sodium bicarbonate, potassium bicarbonate, ammonia and the like; and mixtures thereof. Preferably, the base used is an inorganic base and more preferably potassium carbonate.

The cyclization step iii) may be carried out in presence of an organic solvent, wherein the organic solvent includes, but is not limited to alcohols, amides, aromatic hydrocarbons, halogenated hydrocarbons, nitriles and the like and mixtures thereof. Preferably the solvent used is amides such as dimethylformamide.

The reaction temperature should be sufficient to effect the cyclization reaction. Typically the reaction temperature may be from about ambient temperature to about reflux temperature; preferably about 35° C. to about 110° C.; more preferably at about 80° C. to about 90° C.

Step iv) of the aforementioned process involves hydrolysis of the compound of Formula V, wherein "P" is ethyl and "R" is benzyl; with a base to obtain a protected quinoline carboxylic acid compound of Formula IV, wherein "R" is benzyl.

The base used in step iv) for hydrolysis includes, but is not limited to organic base such as methyl amine, ethyl amine, dimethylamine, diethylamine, triethylamine, N,N-diisopropylethylamine, N,N-dimethylaniline, N,N-dimethyl aminopyridine and the like; an inorganic base such as sodium hydroxide, potassium hydroxide, lithium hydroxide, sodium carbonate, potassium carbonate, lithium carbonate, sodium bicarbonate, potassium bicarbonate, ammonia and the like; and mixtures thereof. Preferably, the base used is an inorganic base and more preferably sodium hydroxide.

The hydrolysis reaction may be carried out at a suitable temperature. The suitable temperature includes at about room temperature to about reflux; preferably at reflux temperature.

The conversion compound of formula IV into ivacaftor of Formula I of step v) can be carried out according to the present invention process described as above.

In another embodiment, the present invention provides an intermediate compound of Formula VI,

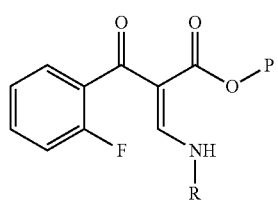

Formula VI wherein "P" represents H or $C_{1-4}$ alkyl and "R" represents a suitable cleavable group; preferably "P" represents H or ethyl and "R" represents a suitable cleavable group selected from aralkyl, alkyl and the like, optionally substituted with one or more groups selected from halo, nitro, cyano, amino, hydroxyl, alkyl, halo alkyl or alkoxy. The aralkyl includes, but are not limited to benzyl, 4-methoxy benzyl, 4-trifluoromethyl benzyl, 4-chloro benzyl and the like; alkyl includes, but is not limited to methyl, ethyl, isopropyl, 1-butyl, n-butyl, t-butyl, 2-methyl-1-propanol, pentyl, 2-pentyl, 3-pentyl, hexyl, heptyl, octyl and the like. Preferably R is benzyl.

In a preferred embodiment, the present invention provides an intermediate compound of Formula VIA.

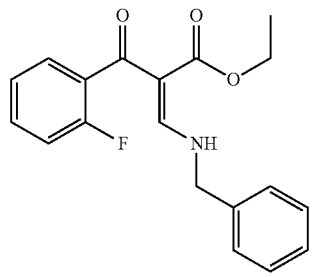

Formula VIA

In another embodiment, the present invention provides an intermediate compound of Formula V,

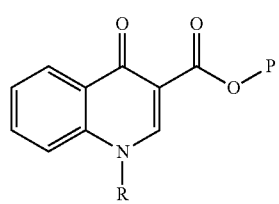

Formula V wherein "P" represents H or $C_{1-4}$ alkyl and "R" represents a suitable cleavable group; preferably "P" represents ethyl and "R" represents a suitable cleavable group selected from aralkyl, alkyl and the like, optionally substituted with one or more groups selected from halo, nitro, cyano, amino, hydroxyl, alkyl, halo alkyl or alkoxy. The aralkyl includes, but are not limited to benzyl, 4-methoxy benzyl, 4-trifluoromethyl benzyl, 4-chloro benzyl and the like; and the alkyl includes, but is not limited to methyl, ethyl, isopropyl, 1-butyl, n-butyl, t-butyl, 2-methyl-1-propanol, pentyl, 2-pentyl, 3-pentyl, hexyl, heptyl, octyl and the like. Preferably R is benzyl.

In a preferred embodiment, the present invention provides an intermediate compound of Formula VA.

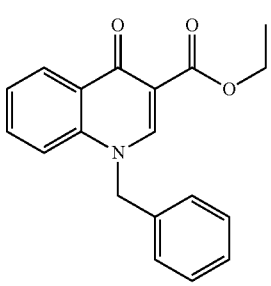

Formula VA

In another embodiment, the present invention provides an intermediate compound of Formula IV,

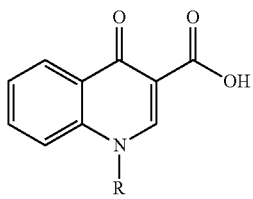

Formula IV wherein "R" represents a suitable cleavable group selected from aralkyl, alkyl and the like, optionally substituted with one or more groups selected from halo, nitro, cyano, amino, hydroxyl, alkyl, halo alkyl or alkoxy; preferably aralkyl includes, but are not limited to benzyl, 4-methoxy benzyl, 4-trifluoromethyl benzyl, 4-chloro benzyl and the like; and the alkyl includes, but is not limited to methyl, ethyl, isopropyl, 1-butyl, n-butyl, t-butyl, 2-methyl-1-propanol, pentyl, 2-pentyl, 3-pentyl, hexyl, heptyl, octyl and the like. Preferably R is benzyl.

In a preferred embodiment, the present invention provides an intermediate compound of Formula IVA.

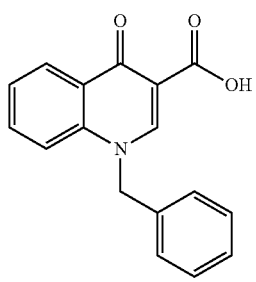

Formula IVA

In another embodiment, the present invention provides a process for the preparation of ivacaftor of formula I, comprising:
a) condensing 2-fluorobenzoylchloride with ethyl-3-N,N-dimethyl amino acrylate in presence of triethylamine in toluene to obtain ethyl-3-(dimethylamino)-2-(2-fluorobenzoyl)-2-propenoate,
b) reacting the ethyl-3-(dimethylamino)-2-(2-fluorobenzoyl)-2-propenoate with benzylamine in toluene to obtain ethyl-3-(benzylamino)-2-(2-fluorobenzoyl)-2-propenoate,
c) cyclizing the ethyl-3-(benzylamino)-2-(2-fluorobenzoyl)-2-propenoate in presence of potassium carbonate in dimethylformamide to obtain ethyl-1-benzyl-4-oxo-1,4-dihydroquinoline-3-carboxylate,
d) hydrolyzing the ethyl-1-benzyl-4-oxo-1,4-dihydroquinoline-3-carboxylate with aqueous sodium hydroxide to obtain 1-benzyl-4-oxo-1,4-dihydroquinoline-3-carboxylic acid,
e) coupling the 1-benzyl-4-oxo-1,4-dihydroquinoline-3-carboxylic acid with 5-amino-2,4-di-(tert-butyl)phenol in presence of HATU and N,N-diisopropylethylamine in dimethylformamide to obtain N-(2,4-di-tert-butyl-5-hydroxyphenyl)-1-benzyl-4-oxo-1,4-dihydroquinoline-3-carboxamide; and
f) deprotecting the N-(2,4-di-tert-butyl-5-hydroxyphenyl)-1-benzyl-4-oxo-1,4-dihydro quinoline-3-carboxamide by treating it with palladium hydroxide and ammonium formate in dimethylformamide to obtain ivacaftor.

In another embodiment, the present invention provides a process for the purification of ivacaftor, comprising dissolving/slurring the ivacaftor in an organic solvent, wherein the organic solvent is selected from the group consisting of alcohols, ethers, esters, ketones, halogenated hydrocarbons, nitriles, amides and the like, and mixtures thereof and isolating the pure ivacaftor. Preferably the solvent used is alcohol and more preferably methanol.

In another embodiment, the present invention provides a process for purification of ivacaftor, which comprises:
a1) dissolving ivacaftor or a solvate thereof in an organic solvent,
b1) partially distilling off the solvent from step a1),
c1) adding an another solvent to the reaction mass of step b1),
d1) partially distilling off the solvent from step c1);
e1) cooling the reaction mass; and
f1) isolating the pure ivacaftor.

The organic solvent used in step a1) is selected from the group consisting of alcohols, ethers, esters, ketones, halogenated hydrocarbons, nitriles, amides and the like, and mixtures thereof; preferably the solvent used is esters and more preferably ethyl acetate.

The solvent used in step d1) is selected from the group consisting of aliphatic hydrocarbon preferably heptane.

In another embodiment, the present invention provides ivacaftor or a pharmaceutically acceptable salt thereof, having purity of at least about 98%, as measured by HPLC; preferably at least about 99%, as measured by HPLC; and more preferably at least about 99.5%, as measured by HPLC.

The reported literature discloses process for the preparation of ivacaftor, which involves high temperature reactions for instance cyclization at about 230° C. ('519 publication) and corrosive reagents such as polyphosphoric acid and phosphoryl chloride in cyclization reaction for the preparation of quinoline carboxylic acid compound of Formula IV. The use of such harsh conditions not only leads to the formation of unwanted by products and low product yields but also makes the process more disadvantageous in both economical and environmental point of view. In contrast, the process herein described by the present invention arrives at ivacaftor, which involves novel protected quinoline compounds as intermediates, thereby avoids such harsh conditions, making the process more suitable for commercial applications.

In another embodiment, the present invention provides a pharmaceutical composition containing ivacaftor or pharmaceutically acceptable salts thereof, disclosed herein and at least one pharmaceutically acceptable excipient. Such pharmaceutical composition may be administered to a mammalian patient in any dosage form, e.g., liquid, powder, elixir, injectable solution, etc.

EXAMPLES

The following non limiting examples illustrate specific embodiments of the present invention. They are not intended to be limiting the scope of the present invention in any way.

Example 1

Preparation of Ethyl-3-(dimethylamino)-2-(2-fluorobenzoyl)-2-propenoate

A flask was charged with 2-fluorobenzoic acid (50.0 g, 0.356 mol) and toluene (500.0 ml, 10.0 vol). Thionyl chloride (84.91 g, 0.713 mol) was added to the reaction mass at 25 to 30° C. The reaction mass was heated to 110° C. and maintained for 12 hours. After completion of reaction, volatiles collected by atmospheric distillation under nitrogen. (Part A, 2-fluorobenzoylchloride). Another flask was charged with ethyl-3-N,N-dimethyl amino acrylate (51.09 g, 0.356 mol), triethylamine (54.71 ml, 0.392 mol) and toluene (250.0 ml, 5.0 vol) and was heated to 50-55° C. A solution of 2-fluorobenzoylchloride obtained above (Part A) in toluene (250.0 ml, 5.0 vol) was added to the reaction mass over a period of 30-60 minutes at 50-55° C. and maintained at same temperature for 12 hours. The reaction mass was cooled to 30° C. and filtered off the salts, washed with toluene (100.0 ml, 2.0 vol). The filtrate was collected, washed with 5% aqueous sodium bicarbonate solution (250.0 ml, 5.0 vol) followed by water and distilled off the solvent under reduced pressure to afford the ethyl-3-(dimethylamino)-2-(2-fluorobenzoyl)-2-propenoate (87.8 g) as a liquid, which was used in the next step without further purification.

$^1$H NMR (CDCl$_3$): δ 7.74 (s, 1H), δ 7.54 (d, 1H), δ 7.3 (m, 1H), δ 7.1 (m, 1H), δ 6.9 (d, 1H), δ 3.9 (q, 2H), δ 3.0 (s, 6H), δ 0.89 (t, 3H); ESI MS: 266 m/z (MH$^+$

Example 2

Preparation of Ethyl-3-(benzylamino)-2-(2-fluorobenzoyl)-2-propenoate

A flask was charged with ethyl-3-(dimethylamino)-2-(2-fluorobenzyl)-2-propenoate (160.0 g, 0.603 mol), toluene (640.0 ml, 4.0 vol) and a solution of benzylamine (64.60 g, 0.603 mol) in toluene (160.0 ml, 1.0 vol) at 25-35° C. The reaction mass was stirred at 25-35° C. for 2 hours. Volatiles were removed by distillation under atmospheric pressure followed by co-distillation with heptane. The solid was filtered off and dried under reduced pressure to afford ethyl-3-(benzylamino)-2-(2-fluorobenzoyl)-2-propenoate (162.0 g).

$^1$H NMR (CDCl$_3$): δ 11.14 (s, 1H), δ 8.15 (d, 1H), δ 7.40 (d, 1H), δ 7.37 (m, 1H), δ 7.10 (m, 3H), δ 7.25 (m, 1H), δ 7.20 (d, 1H), δ 6.9 (d, 2H), δ 4.58 (d, 2H), δ 4.0 (q, 2H), δ 0.98 (t, 3H); ESI MS: 328 m/z (MH$^+$)

Example 3

Preparation of Ethyl-1-benzyl-4-oxo-1,4-dihydroquinoline-3-carboxylate

A mixture of ethyl-3-(benzylamino)-2-(2-fluorobenzoyl)-2-propenoate (100.0 g, 0.305 mol), dimethylformamide (500.0 ml, 5.0 vol) and potassium carbonate (63.30 g, 0.458) was heated to 85-90° C. and stirred for 4 hours. After reaction completion, the reaction mass was cooled to room temperature and water was added to it. The solid obtained was filtered and was washed with water then dried under vacuum to afford ethyl-1-benzyl-4-oxo-1,4-dihydroquinoline-3-carboxylate (77.5 g).

$^1$H NMR (CDCl$_3$): δ 8.60 (s, 1H), δ 7.51 (d, 1H), δ 7.50 (m, 1H), δ 7.30 (d, 2H), δ 7.25 (m, 3H), δ 7.10 (m, 2H), δ 5.39 (s, 2H), δ 4.40 (q, 2H), δ 1.38 (t, 3H); ESI MS: 308 m/z (MH$^+$)

Example 4

Preparation of 1-benzyl-4-oxo-1,4-dihydroquinoline-3-carboxylic acid

Mixture of ethyl-1-benzyl-4-oxo-1,4-dihydroquinoline-3-carboxylate (35.0 g, 0.114 mol) and sodium hydroxide solution (2N, 350.0 ml, 10.0 vol) was heated to reflux temperature and stirred for 2 hours at reflux. After reaction completion, the reaction mass was cooled to room temperature and filtered. The pH of the obtained filtrate was adjusted to 4 with 2N HCl. The precipitated solid was filtered off, washed with water and dried under vacuum to give 1-benzyl-4-oxo-1,4-dihydroquinoline-3-carboxylic acid (29.60 g).

$^1$H NMR (DMSO-d6): δ 15.15 (br s, 1H), δ 9.28 (s, 1H), δ 8.30 (d, 1H) δ 7.80 (d, 2H), δ 7.59 (m, 1H), δ7.30 (m, 5H), δ 5.86 (s, 2H); ESI MS: 280 m/z (MH$^+$)

Example 5

Preparation of N-(2,4-di-tert-butyl-5-hydroxyphenyl)-1-benzyl-4-oxo-1,4-dihydroquinoline-3-carboxamide A mixture of 1-benzyl-4-oxo-1,4-dihydroquinoline-3-carboxylic acid (10.0 g, 0.0358 mol), dimethylformamide (100.0 ml, 10 vol), N,N-diisopropylethylamine (9.25 g, 0.0429 mol), HATU (13.61 g, 0.0358 mol) and 5-amino-2,4-di-tert-butyl phenol (9.51 g, 0.0429 mol) were stirred for 4 hours at 25-30° C. After reaction completion, 5% sodium carbonate solution was added to the reaction mass and stirred. The solid obtained was filtered, washed with water and dried under vacuum at 50-55° C. The dried solid was purified by slurry in methanol (120.0 ml, 12 vol) afforded N-(2,4-di-tert-butyl-5-hydroxyphenyl)-1-benzyl-4-oxo-1,4-dihydroquinoline-3-carboxamide (15.5 g).

$^1$H NMR (DMSO-d6): δ 9.19 (s, 1H), δ 9.17 (s, 1H), δ 7.7 (d, 1H), δ 7.50 (m, 2H), δ 7.49 (d, 1H), δ 7.30 (m, 3H), δ 7.20 (d, 2H), δ 7.1 (s, 1H), δ 5.81 (s, 2H), δ 1.37 (s, 9H), δ 1.34 (s, 9H); ESI MS: 483 m/z (MH$^+$)

Example 6

Preparation of N-(2,4-di-tert-butyl-5-hydroxyphenyl)-4-oxo-1,4-dihydroquinoline-3-carboxamide (Ivacaftor)

To a flask was charged with N-(2,4-di-tert-butyl-5-hydroxyphenyl)-1-benzyl-4-oxo-1,4-dihydroquinoline-3-carboxamide (13.0 g, 0.0269 mol) in dimethylformamide (195.0 mL, 15 vol), 20% palladium hydroxide (13.0 g, 1.0 wt) and ammonium formate (13.0 g, 1.0 wt) was added at 25-30° C. The reaction mass was heated to 70-80° C. and stirred for 3 hours. Then the reaction mass was cooled to 40° C. and filtered. The filtered mass was washed with ethyl acetate. Combined dimethylformamide and ethyl acetate layers were washed with water. The aqueous layer further extracted with ethyl acetate. Both organic layers were combined and washed with water. The organic layer was distilled off under vacuum to a minimum volume and methanol was added to it. The solid obtained was filtered and dried under vacuum at 45° C. to 50° C. To the dried product, ethyl acetate (40 ml) was added and distilled off the solvent to a minimum volume under atmospheric pressure. n-heptane was added to above reaction mass and again distilled off the solvent to a minimum volume under atmospheric pressure. The solid obtained was filtered and dried at 45° C. to 50° C. under vacuum to yield the title compound (8.45 g).

$^1$H NMR (DMSO-d6): δ 12.8 (s, 1H), δ 11.79 (s, 1H), δ 9.17 (s, 1H), δ 8.84 (s, 1H), δ 8.31 (dd, 1H), δ 7.7 (m, 2H), δ 7.4 (m, 1H), δ 7.20 (s, 1H), δ 7.10 (s, 1H), δ 1.36 (s, 9H), δ 1.34 (s, 9H);

HPLC Purity: 99.3% area

Example 7

Purification of Ivacaftor

A mixture of methanol (100 ml, 20 vol) and ivacaftor crude (16 g) was heated to reflux temperature (60-65° C.) and stirred for 60 minutes at reflux. Then the reaction mass was cooled to 25-35° C. over a period of 2 hours. The obtained solid was filtered, washed with methanol (15 ml, 3 vol) and dried at 45-50° C. for 6-8 hours to get the title compound XRPD: 7.00, 8.98, 9.94, 10.54, 10.84, 12.82, 13.56, 13.76, 14.18, 15.00, 15.58, 16.64, 17.74, 18.62, 19.48, 20.18, 20.64, 21.14, 22.14, 21.48, 22.14, 22.72, 23.26, 25.24, 26.24, 26.78, 27.36, 27.94, 28.26, 28.84, 29.42, 30.22, 32.24, 33.82, 35.96 (° 2θ).

Example 8

Purification of Ivacaftor

Ivacaftor obtained from example-7 was dissolved in ethyl acetate (40 vol) and the solvent was distilled off upto 2 volume under atmospheric pressure. Heptane (5 vol) was added to the obtained reaction mass and again distilled off the solvent upto 2 volume under atmospheric pressure. The solid obtained was filtered off and dried (8.45 g, 80.0%) to get the title compound.

XRPD: 5.82, 7.70, 8.68, 9.62, 11.58, 12.36, 13.34, 15.48, 16.40, 17.44, 18.14, 19.04, 19.68, 20.40, 22.50, 23.18, 23.80, 24.72, 25.10, 25.94, 26.68, 27.80, 29.42, 30.26, 31.18, 32.48, 33.12 (° 2θ);

$^1$H NMR (DMSO-d6): δ 12.8 (s, 1H), δ 11.79 (s, 1H), δ 9.17 (s, 1H), δ 8.84 (s, 1H), δ 8.31 (dd, 1H), δ 7.7 (m, 2H), δ 7.4 (m, 1H), δ 7.20 (s, 1H), δ 7.10 (s, 1H), δ 1.36 (s, 9H), δ 1.34 (s, 9H); ESI MS: 393 m/z (MH$^+$);

HPLC Purity: 99.3% area

Example 8

Purification of Ivacaftor

A mixture of ivacaftor methanol solvate (8.80 g) and ethyl acetate (440 ml) was heated to 73-75° C. and stirred for 30 minutes. Ethyl acetate from the reaction mass was distilled off upto 10 volume under atmospheric pressure at 70-75° C. The reaction mass was cooled to 55-60° C. and the solvent was distilled off completely under vacuum. The solid obtained was dried at 55-60° C. and then cooled to 25-20° C. Ethyl acetate (18 ml) was added to the above solid and stirred for 10 mins at 25-30° C. The solid obtained was filtered, washed with ethyl acetate and dried under vacuum at 60-65° C. to get the title compound (8.15 g).

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for the preparation of ivacaftor of Formula I,

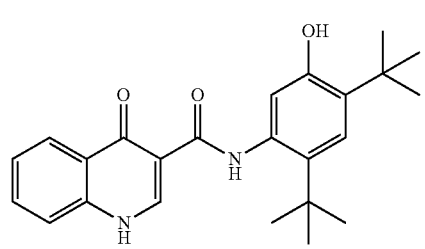

Formula I comprising:
a) coupling a protected quinoline carboxylic acid compound of Formula IV or an ester thereof

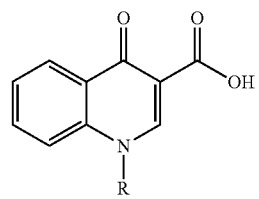

Formula IV wherein "R" represents a cleavable group, with 5-amino-2, 4-di-(tert-butyl) phenol of Formula III

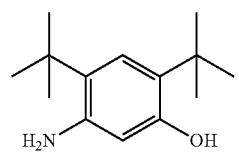

Formula III in the presence of a coupling reagent and optionally in the presence of a base to obtain a protected ivacaftor compound of Formula II

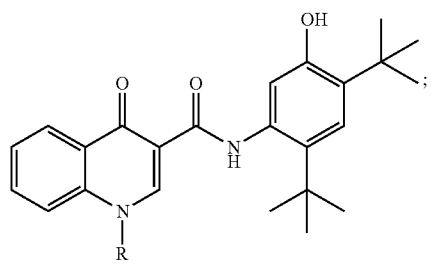

Formula II and
b) deprotecting the resulting protected ivacaftor compound of Formula II.

2. The process according to claim 1, wherein the coupling agent is one of HATU (1-[Bis(dimethylamino)methylene]-1H-1,2,3-triazolo[4,5-b]pyridinium 3-oxid hexafluoro phosphate) and HBTU (O-Benzotriazole-N,N,N',N'-tetramethyl-uronium-hexafluoro-phosphate).

3. The process according to claim 1, wherein the base used in the step a) is one of an organic base and an inorganic base,
  wherein the organic base is one of methyl amine, ethyl amine, dimethylamine, diethylamine, triethylamine, tripropylamine, triisopropylamine, triisobutylamine N,N-diisopropylethylamine, N,N-dimethylaniline, tributylamine, N,N-dimethyl aminopyridine and mixtures thereof; and
  wherein the inorganic base is one of sodium hydroxide, potassium hydroxide, lithium hydroxide, sodium carbonate, potassium carbonate, lithium carbonate, sodium bicarbonate, potassium bicarbonate, ammonia and mixtures thereof.

4. The process according to claim 1, wherein the base is N,N-diisopropylethylamine.

5. The process according to claim 1, wherein the step a) further comprises the presence of an organic solvent selected from the group consisting of alcohols, ethers, esters, nitriles, amides, and mixtures thereof,
  wherein the alcohols is one of methanol, ethanol, isopropanol, n-propanol, n-butanol, isobutanol and t-butanol,
  wherein the ethers is one of dimethyl ether, diethyl ether, methyl ethyl ether, diisopropyl ether, methyl tertiary butyl ether, tetrahydrofuran and 1,4-dioxane,
  wherein the esters is one of ethyl acetate, isopropyl acetate and isobutyl acetate,
  wherein the nitriles is one of acetonitrile and propionitrile, and
  wherein the amide is one of dimethyl formamide, dimethyl acetamide and N-methyl pyrrolidinone.

6. The process according to claim 5, wherein the solvent is dimethyl formamide.

7. The process according to claim 1, wherein the deprotection of formula II is carried out by treating it with a deprotecting agent.

8. The process according to claim 7, wherein the deprotecting agent is selected from one of palladium, raney nickel, hydrazine, hydrochloric acid, hydrobromic acid, trifluoro acetic acid, and mixtures thereof.

9. A process for the preparation of ivacaftor of Formula I, comprising:
  i) condensing 2-fluorobenzoic acid or a reactive derivative thereof of Formula IX

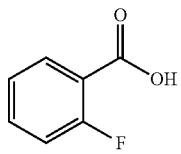

Formula IX with an acrylate compound of Formula VIII

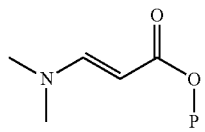

Formula VIII wherein "P" represents H or $C_{1-4}$ alkyl, to obtain a compound of Formula VII

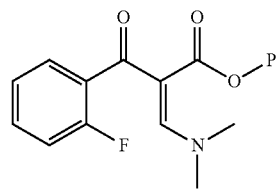

Formula VII wherein "P" is defined as above,
  ii) reacting the compound of Formula VII with an amine of formula R—NH2, wherein "R" represents one of an aralkyl and alkyl group, optionally substituted with one or more of a compound selected from the group consisting of halo, nitro, cyano, amino, hydroxyl, alkyl, halo alkyl and alkoxy, to obtain a compound of Formula VI

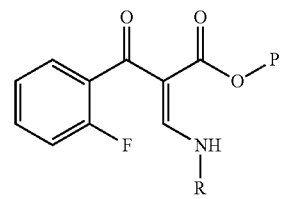

Formula VI wherein "R" and "P" are defined as above;
  iii) cyclizing the compound of Formula VI in the presence of a base to obtain a compound of Formula V

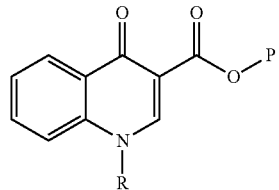

Formula V wherein "R" and "P" are defined as above;
  iv) hydrolyzing the compound of formula V with a base to obtain a protected quinoline carboxylic acid compound of Formula IV,

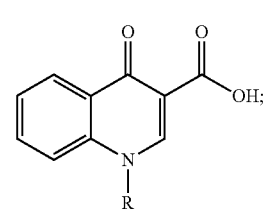

Formula IV and
wherein "R" is defined as above;
  v) converting the protected quinoline carboxylic acid compound of Formula IV into the ivacaftor of Formula I.

10. The process according to claim 9, wherein the step i) is conducted in the presence of a base selected from methyl amine, ethyl amine, dimethylamine, diethylamine, triethylamine N,N-diisopropyl ethyl amine, N,N-dimethylaniline and N,N-dimethyl aminopyridine.

11. The process according to claim 9, wherein in the step ii) the amine of formula, R—NH$_2$ used is one of benzylamine, 4-methoxy benzylamine, 4-trifluoromethyl benzylamine, 4-chloro benzyl amine, ethylamine, isopropylamine, n-butylamine, tert-butylamine, pentylamine, 2-aminopentane, 3-aminopentane, hexylamine, 2-aminohexane, 3-aminohexane, heptylamine, 2-aminoheptane, 3-aminoheptane, 4-aminoheptane, octylamine, 2-amino octane, 3-aminooctane, 4-aminooctane, 2-amino-1-ethanol, 2-amino-2-methyl-1-propanol and 3-amino-1-butanol.

12. The process according to claim 9, wherein in the step iii) the base used for cyclization is one of sodium hydroxide, potassium hydroxide, lithium hydroxide, sodium carbonate, potassium carbonate, lithium carbonate, sodium bicarbonate, potassium bicarbonate, and ammonia.

13. The process according to claim 9, wherein the cyclization of step iii) is carried out at a temperature of about 35° C. to 110° C.

14. The process according to claim 13, wherein the temperature is about 85° C. to 90° C.

15. The process according to claim 9, wherein the base in the step iv) is one of sodium hydroxide, potassium hydroxide, lithium hydroxide, sodium carbonate, potassium carbonate, lithium carbonate, sodium bicarbonate, potassium bicarbonate and ammonia.

16. An intermediate compound of Formula VI, wherein "P" represents H or C$_{1-4}$ alkyl and "R" represents a cleavable group selected from aralkyl, alkyl group, optionally substituted with one or more groups selected from halo, nitro, cyano, amino, hydroxyl, alkyl, halo alkyl or alkoxy.

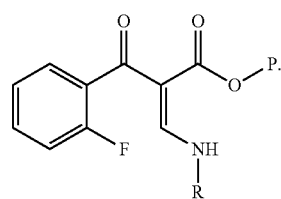

Formula VI

17. An intermediate compound of Formula VIA

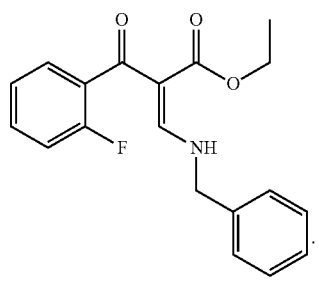

Formula VIA

18. An intermediate compound of Formula II,

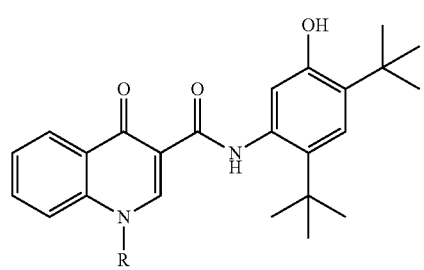

Formula II wherein "R" represents a cleavable group selected from aralkyl, alkyl group, optionally substituted with one or more groups selected from halo, nitro, cyano, amino, hydroxyl, alkyl, halo alkyl or alkoxy.

19. An intermediate compound of Formula IIA

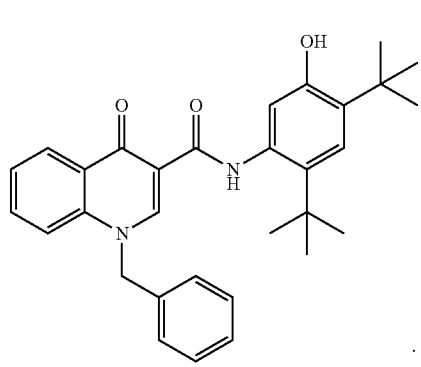

Formula IIA

20. A process for preparation of ivacaftor of Formula I, comprising:
a) condensing 2-fluorobenzoylchloride with ethyl-3-N,N-dimethyl amino acrylate in presence of triethylamine in toluene to obtain ethyl-3-(dimethylamino)-2-(2-fluorobenzoyl)-2-propenoate,
b) reacting the ethyl-3-(dimethylamino)-2-(2-fluorobenzoyl)-2-propenoate with benzylamine in toluene to obtain ethyl-3-(benzylamino)-2-(2-fluorobenzoyl)-2-propenoate,
c) cyclizing the ethyl-3-(benzylamino)-2-(2-fluorobenzoyl)-2-propenoate in presence of potassium carbonate in dimethylformamide to obtain ethyl-1-benzyl-4-oxo-1,4-dihydroquinoline-3-carboxylate,
d) hydrolyzing the ethyl-1-benzyl-4-oxo-1,4-dihydroquinoline-3-carboxylate with aqueous sodium hydroxide to obtain 1-benzyl-4-oxo-1,4-dihydroquinoline-3-carboxyli acid,
e) coupling the 1-benzyl-4-oxo-1,4-dihydroquinoline-3-carboxylic acid with 5-amino-2,4-di-(tert-butyl)phenol in presence of HATU and diisopropylethylamine in dimethylformamide to obtain N-(2,4-di-tert-butyl-5-hydroxyphenyl)-1-benzyl-4-oxo-1,4-dihydroquinoline-3-carboxamide; and
f) deprotecting the N-(2,4-di-tert-butyl-5-hydroxyphenyl)-1-benzyl-4-oxo-1,4-dihydro quinoline-3-carboxamide by treating it with palladium hydroxide and ammonium formate in dimethylformamide to obtain ivacaftor.

21. A process for the preparation of a pharmaceutical composition comprising ivacaftor of Formula I or a pharmaceutically acceptable salt thereof, comprising:

a) coupling a protected quinoline carboxylic acid compound of Formula IV or an ester thereof

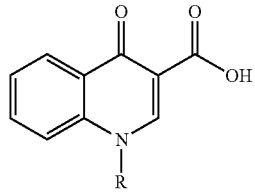

Formula IV wherein R is a cleavable group, with 5-amino-2,4-di-(tert-butyl) phenol of Formula III

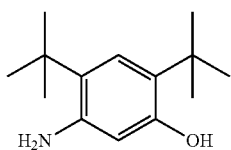

Formula III in the presence of a coupling reagent and optionally in the presence of a base to obtain a protected ivacaftor compound of Formula II

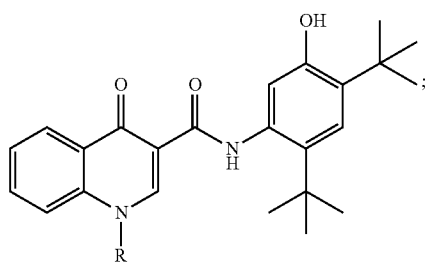

Formula II and b) deprotecting the resulting protected ivacaftor compound of Formula II; and c) combining the ivacaftor of Formula I with at least one pharmaceutically acceptable excipient.

22. A process for the preparation of a pharmaceutical composition comprising ivacaftor of Formula I or a pharmaceutically acceptable salt thereof, comprising:

i) condensing 2-fluorobenzoic acid or a reactive derivative thereof of Formula IX

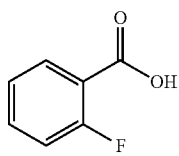

Formula IX with an acrylate compound of Formula VIII

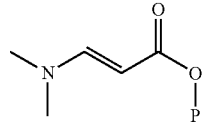

Formula VIII wherein "P" represents H or $C_{1-4}$ alkyl, to obtain a compound of Formula VII

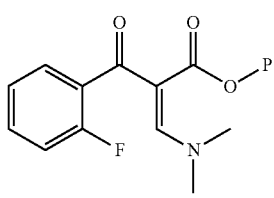

Formula VII wherein "P" is defined as above, ii) reacting the compound of Formula VII with an amine of formula R—NH2, wherein "R" represents one of an aralkyl and alkyl group, optionally substituted with one or more of a compound selected from the group consisting of halo, nitro, cyano, amino, hydroxyl, alkyl, halo alkyl and alkoxy, to obtain a compound of Formula VI

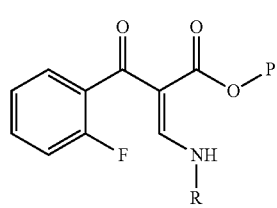

Formula VI wherein "R" and "P" are defined as above;

iii) cyclizing the compound of Formula VI in the presence of a base to obtain a compound of Formula V

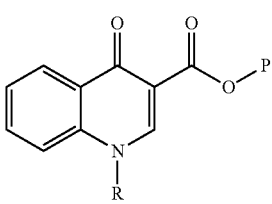

Formula V wherein "R" and "P" are defined as above;

iv) hydrolyzing the compound of formula V with a base to obtain a protected quinoline carboxylic acid compound of Formula IV,

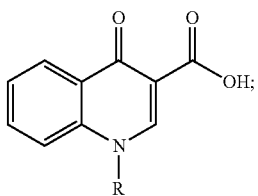

Formula IV and
wherein "R" is defined as above;
  v) converting the protected quinoline carboxylic acid compound of Formula IV into the ivacaftor of Formula I; and
  vi) combining the ivacaftor of Formula I with at least one pharmaceutically acceptable excipient.

23. A process for the preparation of a pharmaceutical composition comprising ivacaftor of Formula I or a pharmaceutically acceptable salt thereof, comprising:
  a) condensing 2-fluorobenzoylchloride with ethyl-3-N,N-dimethyl amino acrylate in presence of triethylamine in toluene to obtain ethyl-3-(dimethylamino)-2-(2-fluorobenzoyl)-2-propenoate,
  b) reacting the ethyl-3-(dimethylamino)-2-(2-fluorobenzoyl)-2-propenoate with benzylamine in toluene to obtain ethyl-3-(benzylamino)-2-(2-fluorobenzoyl)-2-propenoate,
  c) cyclizing the ethyl-3-(benzylamino)-2-(2-fluorobenzoyl)-2-propenoate in presence of potassium carbonate in dimethylformamide to obtain ethyl-1-benzyl-4-oxo-1,4-dihydroquinoline-3-carboxylate,
  d) hydrolyzing the ethyl-1-benzyl-4-oxo-1,4-dihydroquinoline-3-carboxylate with aqueous sodium hydroxide to obtain 1-benzyl-4-oxo-1,4-dihydroquinoline-3-carboxyli acid,
  e) coupling the 1-benzyl-4-oxo-1,4-dihydroquinoline-3-carboxylic acid with 5-amino-2,4-di-(tert-butyl)phenol in presence of HATU and diisopropylethylamine in dimethylformamide to obtain N-(2,4-di-tert-butyl-5-hydroxyphenyl)-1-benzyl-4-oxo-1,4-dihydroquinoline-3-carboxamide;
  f) deprotecting the N-(2,4-di-tert-butyl-5-hydroxyphenyl)-1-benzyl-4-oxo-1,4-dihydro quinoline-3-carboxamide by treating it with palladium hydroxide and ammonium formate in dimethylformamide to obtain ivacaftor; and
  g) combining the ivacaftor of Formula I with at least one pharmaceutically acceptable excipient.

* * * * *